(12) United States Patent
Iwata et al.

(10) Patent No.: US 10,759,141 B2
(45) Date of Patent: *Sep. 1, 2020

(54) STRETCHABLE LAMINATED SHEET

(71) Applicants: JNC CORPORATION, Chiyoda-Ku (JP); JNC FIBERS CORPORATION, Chiyoda-Ku (JP)

(72) Inventors: Junji Iwata, Moriyama (JP); Yasushi Matsuda, Moriyama (JP)

(73) Assignees: JNC CORPORATION, Tokyo (JP); JNC FIBERS CORPORATION, Tokyo (JP)

(*) Notice: Subject to any disclaimer, the term of this patent is extended or adjusted under 35 U.S.C. 154(b) by 71 days.

This patent is subject to a terminal disclaimer.

(21) Appl. No.: 15/331,444

(22) Filed: Oct. 21, 2016

(65) Prior Publication Data

US 2017/0036417 A1  Feb. 9, 2017

Related U.S. Application Data

(63) Continuation of application No. 12/401,292, filed on Mar. 10, 2009, now abandoned.

(30) Foreign Application Priority Data

| Mar. 19, 2008 | (JP) | 2008-072186 |
| Nov. 5, 2008 | (JP) | 2008-284724 |

(51) Int. Cl.
| | |
|---|---|
| B32B 5/04 | (2006.01) |
| B32B 5/26 | (2006.01) |
| B32B 5/02 | (2006.01) |
| B32B 5/06 | (2006.01) |
| D04H 1/559 | (2012.01) |
| A61K 8/02 | (2006.01) |
| A61Q 19/00 | (2006.01) |
| A45D 44/00 | (2006.01) |
| D04H 1/4374 | (2012.01) |

(52) U.S. Cl.
CPC ............ *B32B 5/04* (2013.01); *A45D 44/002* (2013.01); *A61K 8/0208* (2013.01); *A61Q 19/00* (2013.01); *B32B 5/022* (2013.01); *B32B 5/06* (2013.01); *B32B 5/26* (2013.01); *D04H 1/4374* (2013.01); *D04H 1/559* (2013.01); *A61M 2210/0606* (2013.01); *B32B 2262/0253* (2013.01); *B32B 2262/0261* (2013.01); *B32B 2262/0276* (2013.01); *B32B 2262/04* (2013.01); *B32B 2262/062* (2013.01); *B32B 2262/065* (2013.01); *B32B 2262/08* (2013.01); *B32B 2262/14* (2013.01); *B32B 2307/50* (2013.01); *B32B 2307/726* (2013.01); *B32B 2307/728* (2013.01); *B32B 2555/00* (2013.01); *Y10T 428/24331* (2015.01)

(58) Field of Classification Search
None
See application file for complete search history.

(56) References Cited

U.S. PATENT DOCUMENTS

| 8,415,263 B2 * | 4/2013 | Fujiwara | D04H 1/54 |
| | | | 428/103 |
| 10,052,840 B2 * | 8/2018 | Maeda | D04H 1/559 |
| 2003/0003833 A1 | 1/2003 | Kurihara et al. | |
| 2004/0067710 A1 | 4/2004 | Tsujiyama et al. | |
| 2006/0218729 A1 | 10/2006 | Feng et al. | |
| 2007/0042665 A1 | 2/2007 | Peng et al. | |
| 2008/0069845 A1 | 3/2008 | Makihara et al. | |

FOREIGN PATENT DOCUMENTS

| EP | 1813167 | 8/2007 |
| JP | 03-220356 | 9/1991 |
| JP | 9078421 | 3/1997 |
| JP | 10016109 | 1/1998 |
| JP | 10183457 | 7/1998 |
| JP | 2003-020554 | 1/2003 |
| JP | 2003-166161 | 6/2003 |
| JP | 2003250879 | 9/2003 |
| JP | 2004-197291 | 7/2004 |
| JP | 2009228147 | 10/2009 |
| TW | 534868 | 6/2003 |

(Continued)

OTHER PUBLICATIONS

Oxford Dictionaries, "elastomer," Oxford University Press (2010) available at <http://oxforddictionaries.com/definition/english/elastomer?q=elastomer>.

(Continued)

*Primary Examiner* — Dennis J Parad
(74) *Attorney, Agent, or Firm* — Hamre, Schumann, Mueller & Larson, P.C.

(57) ABSTRACT

A stretchable laminated sheet with hydrophilic properties, which particularly has an excellent feeling and stability in wearing and is capable of efficiently enhancing the effect and efficacy brought about by a liquid component on a skin or other object, when the stretchable laminated sheet is impregnated with the liquid component and wet and then used on the skin or other object. A stretchable laminated sheet, which is obtained by partially thermocompression-bonding and laminating a hydrophilic short fiber layer extensible in at least one direction and an microfiber layer having a elastomer long fiber of a fiber diameter of 15 μm or less at 50% or more by weight, wherein discontinuous and regular concave and convex parts caused by the partial thermocompression bonding are formed on a surface of the hydrophilic short fiber layer that is exposed on one surface of the stretchable laminated sheet, the total area of the concave parts is in a range of 3 to 40% of the area of the surface of the hydrophilic short fiber layer, and at least the elastomer long fiber of the microfiber layer is softened and consequently joined to a fiber constituting the hydrophilic short fiber layer in a sheet thickness direction of a section where the concave parts exist, whereby the hydrophilic short fiber layer and the microfiber layer are integrated with each other.

13 Claims, No Drawings

(56) References Cited

FOREIGN PATENT DOCUMENTS

| TW | I297051 | 5/2008 |
|----|---------|--------|
| TW | I301166 | 9/2008 |
| WO | 9732567 | 9/1997 |
| WO | 2006016601 | 2/2006 |

OTHER PUBLICATIONS

Merriam-Webster, "elastomer," Merriam-Webster.com, Encyclopaedia Britannica (2013) available at <http://www.merriam-webster.com/dictionary/elastomer>.
Oxford English Dictionary, "elastomer,n.", OED Online, Oxford University Press (2012) available at <http://www.oed.com/view/Entry/60138?redirectedFrom=elastomer>.
The Extended European Search Report issued in European application No. 09003742.5, dated Jun. 25, 2009, total 5 pages.
Office Action issued in Japanese application 2008-284724, dated Jun. 11, 2012, Japanese only, total 3 pages.

\* cited by examiner

STRETCHABLE LAMINATED SHEET

BACKGROUND OF THE INVENTION

Field of the Invention

The present invention relates to a stretchable laminated sheet having a hydrophilic layer, and to a product obtained using the stretchable laminated sheet.

Description of the Related Art

Various types of fibers including cellulosic fiber have conventionally been known as hydrophilic fibers. Because of their hydrophilic properties, these fibers have been used in absorbent articles, cleaning supplies, cosmetic sheets, and the like. Especially when used on a human skin, the important required performance is the texture and the fitting feeling of a product obtained using such hydrophilic fibers. However, a conventionally used cellulosic non-woven fiber has rough and hard feeling and lacks in texture and fitting feeling.

As an example of a sheet applied onto a skin, there is proposed a face mask in which a hydrophilic fiber layer is practically interlaced by water flow with a microfiber layer obtained by dividing a splittable type conjugate fiber consisting of a non-elastomer, and the microfiber layer is taken as a contact surface contacting with a skin, reducing the stimulation to the skin and improving the wearability for the skin (see International Publication WO 2006/016601 pamphlet, for example).

DISCLOSURE OF THE INVENTION

Problem to be Solved by the Invention

An object of the present invention is to provide a stretchable laminated sheet having hydrophilic properties. Particularly, an object of the present invention is to provide a stretchable laminated sheet which has an excellent feeling and stability in wearing and is capable of efficiently enhancing the effect and efficacy brought about by a liquid component on a skin or other object, when the stretchable laminated sheet is impregnated with the liquid component and then used on the skin or other object. Another object of the present invention is to provide a product obtained using this stretchable laminated sheet.

Means to Solve the Problem

As a result of many keen studies conducted by the inventors in order to solve the above problems, the inventors have found out that the problems could be solved by a stretchable laminated sheet that is obtained by partially integrating a hydrophilic short fiber layer extensible in at least one direction with a microfiber layer having at least a certain amount of elastomer long fiber having a fiber diameter of 15 μm or less, by thermally compression-bonding them. The inventors therefore have completed this invention.

Therefore, the present invention has the following configurations:

(1) A stretchable laminated sheet, which is obtained by partially thermocompression-bonding to laminate a hydrophilic short fiber layer extensible in at least one direction and an microfiber layer having an elastomer long fiber of 15 μm or less at 50% or more by weight based on the microfiber layer, wherein discontinuous and regular concave and convex parts caused by the partial thermocompression bonding are formed on a surface of the hydrophilic short fiber layer that is exposed on one surface of the stretchable laminated sheet, the total area of the concave parts is in a range of 3 to 40% of the area of the surface of the hydrophilic short fiber layer, and at least the elastomer long fiber of the microfiber layer is softened and consequently joined to a fiber constituting the hydrophilic short fiber layer in a sheet thickness direction of a section where the concave parts exist, whereby the hydrophilic short fiber layer and the microfiber layer are integrated with each other.

(2) The stretchable laminated sheet described in (1) above, wherein a surface of the microfiber layer exposed on another surface of the stretchable laminated sheet is smooth.

(3) The stretchable laminated sheet described in (1) or (2) above, wherein when 100 parts by weight of the stretchable laminated sheet is impregnated with 100 to 1500 parts by weight of the liquid component, an elongation recovery ratio is in a range of 30 to 100% after the stretchable laminated sheet is extended in the at least one direction by 30%.

(4) The stretchable laminated sheet described in any of (1) to (3) above, wherein the hydrophilic short fiber layer has at least 30% by weight of the short fiber comprising cotton, rayon, cuprammonium, pulp, or two or more of them.

(5) The stretchable laminated sheet described in any of (1) to (4) above, wherein the hydrophilic short fiber is a spunlace non-woven fabric or a wetlaid web.

(6) The stretchable laminated sheet described in any of (1) to (5) above, wherein the microfiber layer is a fiber layer obtained by randomly accumulating long fibers produced by a melt blow method.

(7) The stretchable laminated sheet, wherein 100 parts by weight of the stretchable laminated sheet described in any of (1) to (6) above is impregnated with 100 to 1500 parts by weight of drug solution or cosmetics.

(8) A product, which is obtained by using the stretchable laminated sheet described in any of (1) to (7) above.

The stretchable laminated sheet of the present invention brings an excellent feeling and stability in wearing on a skin and the like, especially when impregnated with a liquid component and then used on the skin or other object.

According to the configuration of the stretchable laminated sheet of the present invention, the hydrophilic short fiber layer and the microfiber layer having an elastomer fiber are integrated by being partially thermocompression-bonded, so that interlayer peeling resistance or other strength that is required in the laminated sheet can be secured. Therefore, the wet laminated sheet that is impregnated with the liquid component can realize an excellent stretchability. In addition, the effect and efficacy brought about by the liquid component on the skin or other object can be improved efficiently.

Therefore, the stretchable laminated sheet of the present invention can be suitably used in a face mask or the like that is impregnated with drug solution or cosmetics.

DESCRIPTION OF THE PREFERRED EMBODIMENTS

The present invention is now described hereinafter in detail based on the embodiments of the present invention.

The stretchable laminated sheet of the present invention has a hydrophilic short fiber layer and a microfiber layer.

The hydrophilic short fiber layer used in the present invention is extensible in at least one direction. Examples of this fiber layer include a card web having unidirectionally-aligned short webs, an air laid web or wetlaid web having randomly accumulated short webs, and a non-woven fabric that is obtained three-dimensionally interlacing these fibers by means of a needle punch or spunlace (interlacing by water flow) method. The wetlaid web or a spunlace non-woven fabric is preferred. In the present invention, the spunlace non-woven fabric is particularly preferred in terms of realizing an excellent stretchability that is obtained especially when the spunlace non-woven fabric is laminated with microfiber layer defined in the present invention and is in a wet state, the spunlace non-woven fabric being obtained by means of interlacing by water fluid a card web having unidirectionally-aligned short webs and then three-dimensionally interlacing these fibers.

Although not particularly limited, the length of the short fibers constituting the hydrophilic short fiber layer is preferably 2 to 100 mm. As the fibers constituting the hydrophilic short fiber layer, short fibers with the typically used length can be used in accordance with a specific method for preparing a fiber layer or in accordance with, for example, a card web, air laid web, wetlaid web, and the like.

In the present invention, if the hydrophilic fiber layer is constituted by long fibers or continuous fibers, the fibers interfere or get entangled with each other, which limits the degrees of freedom of the fibers. As a result, it becomes difficult to produce extensibility that can follow the shrinkability caused by the elastomer fibers of the microfiber layer integrated with the hydrophilic fiber layer. Constituting the hydrophilic fiber layer with the short fibers reduce the interference between the fibers and increases the degrees of freedom of the fibers. As a result, the hydrophilic fiber layer can realize the followability (extensibility) that can sufficiently reflect the stretchability of the microfiber layer to the laminated sheet.

Examples of the short fibers constituting the hydrophilic short fiber layer include cellulose fibers such as cotton and hemp, wool, silk, rayon, cuprammonium, pulp, semisynthetic fibers obtained by using cellulose, and hydrophilized synthetic fibers. Two or more types of these fibers may be used. Cotton, rayon, cuprammonium, and pulp are preferred in terms of hydrophilic properties. It is preferred that the hydrophilic short fiber layer have 30% or more of these hydrophilic short fibers by weight in order to retain a sufficient amount of drug solution or cosmetics or to secure an appropriate penetration speed of the drug solution or cosmetics. It is preferred that the hydrophilic short fiber layer particularly have cotton, rayon, cuprammonium, pulp, or a combination of at least two of these fibers at 30% or more by weight of the hydrophilic short fiber layer.

It is particularly preferred that the hydrophilic short fiber layer be constituted by these hydrophilic short fibers only, in order to be able to retain the higher amount of drug solution or cosmetics in the laminated sheet or to increase the penetration speed of the drug solution or cosmetics. Fibers other than the abovementioned hydrophilic short fibers may be mixed in the hydrophilic short fiber layer at no more than 70% by weight of the hydrophilic short fiber layer, in order to appropriately and efficiently adjust the retention capability or penetration speed of the drug solution or cosmetics within the laminated sheet, as well as the mechanical strength or the degree of extensibility of the hydrophilic short fiber layer. Especially when the hydrophilic short fiber layer contains the fibers other than the hydrophilic short fibers at a range of 30 to 50% by weight of the hydrophilic short fiber layer, the retention capability or penetration speed of the drug solution or cosmetics within the laminated sheet can be increased significantly, while keeping the mechanical strength or the degree of extensibility of the hydrophilic short fiber layer at a proper level. On the other hand, when increasing the mechanical strength and the degree of extensibility of the hydrophilic short fiber layer or laminated sheet while keeping the retention capability or penetration speed of the drug solution or cosmetics within the laminated sheet, it is preferred that the hydrophilic short fiber layer contain the fibers other than the hydrophilic short fibers at a range of 50% to 70% by weight of the hydrophilic short fiber layer. Examples of the fibers to be mixed include water-repellent synthetic fibers such as fibers obtained using polyester, polyolefin, polyamide, or conjugate fibers obtained by combining at least two types of these polymers.

Although not particularly limited, the cross-sectional shape of each of the fibers contained in the hydrophilic short fiber layer can be round, flat, non-circular, or hollow. When each of the fibers of the hydrophilic fiber layer has a round cross-sectional shape, the fiber diameter is preferably larger than 15 µm but less than or equal to 50 µm.

It is preferred that the mass per unit area of the hydrophilic short fiber layer be 5 to 95 $g/m^2$ in terms of the strength of the stretchable laminated sheet, the impregnated amount (retaining amount) of the liquid component, and the stretchability obtained when the stretchable laminated sheet is impregnated with the liquid component. The mass per unit area of the hydrophilic short fiber layer is preferably in a range of 10 to 70 $g/m^2$. The thickness of the hydrophilic short fiber layer is preferably at least 20% on the basis of the thickness of the stretchable laminated sheet, and is more preferably 30 to 95% in order to secure a sufficient impregnated amount and sufficient stretchability in the stretchable laminated sheet when impregnating it with the liquid component.

In addition, the degree of extensibility of the hydrophilic short fiber layer in the dry state is preferably 20 to 250% and more preferably 20 to 200%, in order to secure the extensibility of the stretchable laminated sheet.

The microfiber layer of the stretchable laminated sheet of the present invention has an elastomer long fiber having a fiber diameter of 15 µm or less. It is more preferred that the fiber diameter of the elastomer long fiber be 10 µm or less, because the stretchable laminated sheet having the microfiber layer becomes more flexible and more excellent wearing feeling is obtained on a skin or the like especially when the stretchable laminated sheet is impregnated with the liquid component.

Examples of an elastomer material to be used in the elastomer long fiber include styrene elastomer, olefinic elastomer, ester elastomer, urethane elastomer, and a mixture thereof. Styrene elastomer, olefinic elastomer, and urethane elastomer are particularly preferred in terms of the wearing feeling associated with the flexibility and stretchability of the stretchable laminated sheet impregnated with the liquid component, and the wearing stability associated with the stretchability or the like of this stretchable laminated sheet.

Two or more types of these elastomer long fibers may be mixed together within the microfiber layer. Examples of such a mixture include a mixture of 1 to 99 wt % of a styrene elastomer long fiber and 99 to 1 wt % of an olefinic elastomer long fiber, a mixture of 1 to 99 wt % of an urethane elastomer long fiber and 99 to 1 wt % of an olefinic elastomer long fiber, and a mixture of 1 to 99 wt % of an olefinic elastomer long fiber and 99 to 1 wt % of another olefinic elastomer long fiber. Of these mixtures, examples of a specific mixture of two olefinic elastomer long fibers include a mixture of a polypropylene elastomer long fiber and another polypropylene elastomer long fiber, a mixture of a polypropylene elastomer long fiber and a polyethylene elastomer long fiber, and a mixture of a polyethylene elastomer long fiber and another polyethylene elastomer long fiber. Especially the wearing feeling associated with the flexibility and stretchability of the stretchable laminated sheet impregnated with the liquid component, and the wearing stability associated with the stretchability or the like of this stretchable laminated sheet can be adjusted within a desired range at a high level, depending on the types and weight ratio of the elastomer long fibers to be mixed.

The wearing feeling associated with the flexibility and stretchability of the stretchable laminated sheet impregnated with the liquid component, and the wearing stability associated with the stretchability or the like of this stretchable laminated sheet can be adjusted/controlled at a high level by selecting and mixing, as the fibers constituting the microfiber layer, a styrene elastomer long fiber and olefinic elastomer long fiber having a fiber diameter of 15 µm or lower or preferably 10 µm or lower. It is preferred that the styrene elastomer long fiber and the olefinic elastomer long fiber be mixed evenly and randomly. Specifically, the wearing feeling associated with the flexibility and stretchability of the stretchable laminated sheet impregnated with the liquid component, and the wearing stability associated with the stretchability or the like of this stretchable laminated sheet can be adjusted/controlled at a higher level by using the microfiber layer in which a mixing ratio between 30 to 70 wt % of the styrene elastomer long fiber and 70 to 30 wt % of the olefinic elastomer long fiber is appropriately set at a desired value.

Compared to a conventional stretchable laminated sheet, the stretchable laminated sheet of the present invention exerts an excellent flexibility and particularly a excellent stretch performance when it is wet. Due to such performances, the stretchable laminated sheet of the present invention is suitably used in, for example, a face mask to be impregnated with drug solutions or cosmetics and applied onto a skin. A certain section of the skin on which the face mask is applied is moisturized or moistened by the drug solution or cosmetics. As a result, the surface of the skin becomes sensitive and delicate.

Although the styrene elastomer long fiber generally has an excellent flexibility, it is somewhat excessively viscous. As a result, there may be a case that the adhering of the sheet to the skin is felt too strong, depending on the section of the skin to which the sheet applied or the kind of the liquid component with which the stretchable laminated sheet is impregnated. Moreover, the styrene elastomer long fiber has a sufficient high stretchability, which pulls the skin as the sheet on the skin shrinks after applying onto the skin and causes skin tightness. Consequently, it may not be possible to obtain a comfortable wearing feeling, depending on the section of the skin or the amount of liquid component to impregnate the stretchable laminated sheet. Therefore, mixing the olefinic elastomer long fiber at a specific ratio within the abovementioned range can provide extremely soft and comfortable wearing feeling to the section of the sensitive and delicate skin on which the stretchable laminated sheet is applied. The laminated sheet to be used, and particularly the structure of the microfiber layer may be appropriately adjusted by the ingredients or properties of the drug solution or cosmetics for impregnating the laminated sheet. For example, in the case where there is concern that the oil content of the drug solution or cosmetics might cause swelling or the like of the microfiber layer, it is preferred that the microfiber layer be constituted by fibers having olefinic elastomer as the main fiber, or particularly a mixture of the olefinic elastomer long fiber and another olefinic elastomer long fiber.

A stabilizer, flame retardant, antibacterial agent, colorant, lubricant, light-resistant agent, hydrophilic agent, antistatic agent, charging agent, and the like may be added to the microfiber used in the present invention, as long as the effects of the present invention are not impaired.

The microfiber layer used in the stretchable laminated sheet of the present invention may include fibers other than "the elastomer long fibers having a fiber diameter of 15 µm or less." It is preferred that the elastomer long fibers having a fiber diameter of 15 µm or less be included at 50% or more by weight of the microfiber layer, in order to obtain a comfortable wearing feeling associated with the flexibility and stretchability of the stretchable laminated sheet, and the wearing stability associated with the stretchability or the like of the stretchable laminated sheet. Preferably, the elastomer long fibers are included at 70% or more by weight of the microfiber layer. It is particularly preferred to constitute the microfiber layer with such elastomer long fibers only in order to obtain a stretchable laminated sheet having high levels of wearing feeling and wearing stability.

Examples of the fibers other than "the elastomer long fibers having a fiber diameter of 15 µm or less" include elastomer fibers having a fiber diameter of larger than 15 µm but less than or equal to 50 µm, and non-elastomer fibers such as polyester, polyolefin, and polyamide. Using "the elastomer long fibers having a fiber diameter of 15 µm or less" along with 1 to 50 wt % of non-elastomer fibers having a fiber diameter of 1 to 15 µm is effective in appropriately and efficiently adjusting the wearing feeling or wearing stability associated with the flexibility or stretchability of the stretchable laminated sheet to be obtained, although the stretchable laminated sheet is not as excellent as that obtained by combining a different type of elastomer fibers at a specific ratio. Examples of the non-elastomer fibers to be used include polyester terephthalate, polypropylene, polyethylene, nylon 6, and nylon 66. At least some of the fibers constituting the microfiber layer may have hydrophilic properties, under the condition that the hydrophilic properties of the microfiber layer is not greater than the hydrophilic properties of the hydrophilic short fiber layer. Examples of the hydrophilic fibers to be used include cellulose fibers such as cotton and hemp, wool, silk, rayon, cuprammonium, semisynthetic fibers obtained by using cellulose, and hydrophilized synthetic fibers.

The method of producing the elastomer long fibers used in the microfiber layer and having a fiber diameter of 15 µm or less is not limited, as long as the fiber diameter is 15 µm or less. More specifically, it is preferred that the elastomer long fibers be accumulated randomly in the microfiber layer so that the stretchability of the elastomer long fibers is produced/reflected not unidirectionally but evenly in the laminated sheet. In the fiber layer having unidirectionally-aligned elastomer long fibers, although the stretchability of the fibers is reflected smoothly in a direction same as the length direction of the fibers, the stretchability of the fibers is not produced in a direction perpendicular to the length direction.

The elastomer long fibers are preferably produced by a melt blow method, and it is preferred that the microfiber layer have elastomer long fibers having a fiber diameter of 15 µm or less which are produced by a melt blow method and accumulated randomly. Unlike a general production method in which a surfactant is attached to the surface of each fiber in order to prevent a problem caused by electrostatic charge on the fiber occurred in the process of producing the fiber layer, it is not necessary to attach a surfactant in the melt blow method. Therefore, employing the melt blow method can efficiently produce water-repellent fibers that are suitably used in the microfiber layer.

The method of mixing "the elastomer long fibers having a fiber diameter of 15 μm or less" used in the microfiber layer with "other fibers" is not particularly limited. These fibers may be mixed together after producing them individually. It is also preferred to employ a method for using a so-called nozzle for mixed fibers in which spinning holes for discharging different types of fibers are aligned alternately, to spin these different types of fibers simultaneously by means of the melt blow method. This method can obtain the microfiber layer having different types of fibers accumulated extremely evenly and randomly.

When the microfiber layer has 0 to 10 wt % of non-elastomer long fibers and 100 to 90 wt % of elastomer long fibers, and especially when the microfiber layer is constituted by elastomer long fibers only and the elastomer long fibers are mixed fibers of two or more types of elastomer long fibers, or particularly mixed fibers of 30 to 70 wt % of styrene elastomer long fibers and 70 to 30 wt % of olefinic elastomer long fibers, it is preferred that these two or more types of fibers be spun by the melt blow method using the nozzle for mixed fibers described above.

When using such elastomer long fibers that can produce high degree of delicate performance, such as extremely comfortable wearing feeling associated with a high degree of flexibility and stretchability of the stretchable laminated sheet, and high and appropriate degree of wearing stability associated with the stretchability, the delicate performance is suitably secured depending on the elastomer long fibers to be used or on whether the two or more types of elastomer long fibers are accumulated/mixed in the microfiber layer evenly and randomly.

The structure of the nozzle for mixed fibers is not particularly limited as long as it can spin different types of fibers simultaneously and accumulate them evenly and randomly. As the nozzle for mixed fibers, a nozzle in which spinning holes for letting out different types of fibers are lined up alternately or in a zigzag manner can be suitably used. In another example, a device in which a plurality of nozzles with respective spinning holes for respectively letting out resins are aligned in a moving direction of an accumulation conveyor can be used to spin the different resins from the respective nozzles and then interlace thus obtained web by means of a needle punch or the like in order to mix the fibers. The nozzle that has spinning holes for letting out different types of resins and the spinning holes are aligned alternately therein are used preferably due to needless of post-processing.

It is preferred that the mass per unit area of the microfiber layer be 5 to 100 g/m$^2$ so that an excellent elongation recovery ratio can be obtained when the stretchable laminated sheet is moistened. It is further preferred that the mass per unit area of the microfiber layer be 10 to 70 g/m$^2$. The thickness of the microfiber layer is preferably 80% or less on the basis of the thickness of the stretchable laminated sheet and more preferably 5 to 70% so that a suitable flexibility and wearing feeling can be secured in the stretchable laminated sheet.

The hydrophilic short fibers used in the hydrophilic short fiber layer generally absorb the liquid thereinto by themselves. Therefore, when a non-woven fabric sheet constituted only by hydrophilic fibers is impregnated with drug solution or cosmetics, the non-woven fabric needs to be filled with the drug solution or cosmetics in an amount greater than that required actually on a skin, because the fibers themselves absorb the liquid thereinto. In this case, therefore, the use efficiency of the drug solution or cosmetics becomes low, causing an increase in costs.

However, because the stretchable laminated sheet of the present invention is integrated by partially thermocompression-bonding the hydrophilic short fiber layer and the microfiber layer having elastomer long fibers 50% or more by weight, as described hereinafter, interlayer peeling resistance or other strength required in the laminated sheet can be secured sufficiently. Therefore, the stretchable laminated sheet can be thinned in accordance with the strength required by the product. Consequently, the absolute amount of the drug solution or cosmetics absorbed by the hydrophilic fibers of the laminated sheet can be reduced, and the effective amount of the drug solution or cosmetics can be efficiently supplied to the skin.

Moreover, the efficient use of the drug solution or cosmetics can be also achieved by mixing the fibers other than the hydrophilic fibers into the hydrophilic short fiber layer at no more than 70 wt %. On the other hand, together with the lamination of the microfiber layer, the amount of the drug solution or cosmetics retained in the stretchable laminated sheet itself and the speed of the drug solution or cosmetics penetrating into the stretchable laminated sheet tend to decrease. However, the retaining amount and the penetration speed can be adjusted by mixing the hydrophilic fibers into the microfiber layer at no more than 50 wt % under the condition that the hydrophilic properties of the hydrophilic short fiber layer is greater than the hydrophilic properties of the microfiber layer. The abovementioned examples of the hydrophilic can be also used as the hydrophilic fibers to be mixed into the microfiber layer. According to these methods, the total amount of the hydrophilic fibers of the stretchable laminated sheet can be reduced, while maintaining the retaining amount or penetration speed of the drug solution or cosmetics within a desired range. Therefore, the drug solution or cosmetics can be used effectively, contributing to cost reduction.

In the stretchable laminated sheet of the present invention, the hydrophilic short fiber layer and the microfiber layer are laminated by being partially thermocompression-bonded. Examples of general fiber layer laminating means include a method of using a heating roll, heating oven method, needle punch method, spunlace method (interlacing by water flow), method of using ultrasonic waves, method of fusing an adhesive, and the like.

Although not particularly limited, the partial thermocompression bonding that is performed when producing the stretchable laminated sheet of the present invention can be suitably performed by using a heating roll (to be sometimes referred to as "heating emboss roll" hereinafter) having an embossed roll surface. In the present invention, the partial thermocompression bonding performed using the emboss roll is carried out by pressure-bonding the heating emboss roll to a surface on the hydrophilic short fiber layer side that is exposed on one of the surfaces of the laminated sheet. At this moment, the other surface of the laminated sheet, i.e., a surface on the microfiber layer side that is exposed on the other surface of the laminated sheet, is in contact with a roll or the like that has a flat or embossed surface that may be heated. The surface of the hydrophilic short fiber layer that is exposed on one of the surfaces of the laminated sheet has regular concave and convex shape formed discontinuously as a result of the partial thermocompression bonding. On the other hand, the surface of the microfiber layer that is exposed on the other surface of the stretchable laminated sheet preferably has a flat surface that is formed by coming into contact with a smooth roll.

In the stretchable laminated sheet of the present invention, the concave and convex parts formed by the abovementioned partial thermocompression bonding on the surface of the hydrophilic short fiber layer that is exposed on one of the surfaces of the sheet are such that the total area of the concave parts (to be sometimes referred to as "pressure-bonded area" hereinafter) is within a range of 3 to 40% of the area of the surface of the hydrophilic short fiber layer. The pressure-bonded area in this range is preferred in terms of the interlayer strength and soft touch feeling of the laminated sheet. It is more preferred that the pressure-bonded area be within a range of 5 to 30%.

Moreover, also the discontinuous and regular concave and convex parts which may be formed by the partial thermocompression bonding on the surface of the microfiber layer that is exposed on the other surface of the laminated sheet are such that the area of the concave parts (pressure-bonded area) may be within a range of 3 to 40% of the area of the surface of the microfiber layer.

It is preferred that the depth of each concave part on each surface of the laminated sheet be 0.1 to 1 mm in terms of the interlayer strength and soft touch feeing of the laminated sheet, the area of each concave part be 0.15 to 15 mm$^2$, and the distance between the concave parts be 0.5 to 20 mm.

In the stretchable laminated sheet of the present invention, at least the elastomer long fiber of the microfiber layer is joined to a fiber constituting the hydrophilic short fiber layer in a sheet thickness direction of sections where the concave parts exist, by softening the elastomer long fiber, whereby the hydrophilic short fiber layer and the microfiber layer are integrated with each other. The pressure and temperature at the time of partial thermocompression bonding can be appropriately selected under the condition that the hydrophilic short fiber layer and the microfiber layer are integrated by softening the elastomer long fiber of the microfibers, and the pressure is preferably within a range of 5 to 100 kg/cm$^2$ at the time of the partial thermocompression bonding, and the temperature 50 to 150° C. at the time of the thermocompression bonding. The pressure and temperature are not particularly limited as long as the abovementioned joining is carried out between the microfiber layer and the hydrophilic short fiber layer and the interlayer strength can be obtained.

As described above, according to the present invention, the hydrophilic layer has to be a short fiber layer, as it can follow the stretchability of the microfiber layer. The laminated sheet of the present invention is characterized in that an excellent stretchability can be exceptionally generated especially in a direction of the extensibility of the hydrophilic short fiber layer, when the laminated sheet is in a wet state rather than the dry state. It is expected that the reason is because interference/entanglement caused by the hydrophilic short fibers or between the hydrophilic short fibers is reduced by moistening the laminated sheet. However, when the interference/entanglement between the short fibers is reduced, consequently the strength of the hydrophilic short fiber layer itself is attenuated, which might rupture the fiber layer easily.

It is effective to employ "a partial thermocompression bonding method" as a method for integrating the both layers in the present invention, in order to maintain the balance between the followability of the hydrophilic short fiber layer to the stretchability of the microfiber layer and the strength of the hydrophilic short fiber layer. According to the partial thermocompression bonding method, because the fibers are strongly joined to each other by thermally softening the fibers in the "pressure-bonding part," peeling resistance between the microfiber layer and the hydrophilic short fiber layer can be strengthened. On the other hand, because the individual fibers exist unboundedly in a "non-pressure-bonding part" formed along with the "pressure-bonding part" by employing the partial thermocompression bonding method, the stretchability of an obtained laminated sheet can be produced mainly by the elongation of the fibers of this section. The followability based on the extensibility of the hydrophilic short fiber layer with respect to the stretchability of the microfiber layer, and the excellent stretchability of the resulting laminated sheet are secured by reinforcing the interlayer peeling resistance by means of the "pressure-bonding part." Specifically, if the integration of the both layers is weak, the hydrophilic short fiber layer is peeled easily before sufficiently following the stretchability of the microfiber layer. It is considered that the laminated sheet of the present invention generates an excellent stretchability especially when it is wet, because the interference/entanglement between the hydrophilic short fibers present in the "non-pressure-bonding part" is reduced and the followability of the hydrophilic short fiber layer to the stretchability of the microfiber layer is further enhanced.

The elastomer long fiber contained in the microfibers is softened by means of heat pressure bonding and joined to the fibers constituting the hydrophilic short fiber layer, whereby the both layers are integrated with each other. At this moment, in addition to the bonding force generated by softening the elastomer long fiber, the bonding force between the elastomer long fiber and the fibers constituting the hydrophilic short fiber layer is reinforced by the sticking force or adhesion force inherent to the elastomer long fiber, so that the interlayer peeling resistance is further strengthened.

This integration accompanied by the strong joining can provide a laminated sheet that cannot be ruptured easily even when highly stretched. As described above, in the present invention, the fact that at least the hydrophilic fiber layer is constituted by short fibers, that the microfiber layer has the elastomer fibers, and that the both layers are integrated by being partially thermocompression-bonded to each other forms a foundation for achieving the effects of the present invention.

In a laminated sheet in which the layers are integrated by simply three-dimensionally interlacing fibers by the spunlace method (interlacing by water flow) or needle punch method, it is considered that interference/entanglement between the short fibers at the three-dimensional interlacing points can be reduced in wet state. However, in the laminated sheet in which the layers are integrated by three-dimensionally interlacing the fibers, interlacing between the fibers at the interlacing points integrating the layers is loosened, whereby the layers are peeled easily before sufficient followability of the hydrophilic short fiber layer to the stretchability of the microfiber layer is generated.

In addition, when the layers are integrated using the spunlace method (interlacing by water flow) or needle punch method, high-pressure water or a needle to be used penetrates or passes through the laminated body, whereby the fibers are shifted toward the periphery of the penetrated section and rearranged. Therefore, the air permeability of the laminated body having the integrated layers becomes higher than that obtained before the layer integration, as the distance between the fibers in the penetrated or passed section increases.

On the other hand, integrating the layers using the partial thermocompression bonding method joins the fibers together at the bonded section by softening the elastomer fibers contained at least in the microfiber layer. In other words, the space between the fibers are closed by press and softening the elastomer fibers, hence the air permeability of the laminated body having the integrated layers becomes lower than that obtained before the layer integration.

In the stretchable laminated sheet of the present invention, integrating the layers using the partial thermocompression bonding method effectively reduces the air permeability of the sheet. As a result, in the case where the laminated sheet is impregnated with the drug solution or cosmetics and applied to a skin or the like while the laminated sheet is wet, high masking effect or wrapping effect is produced, efficiently improving the effect and efficacy brought about by the drug solution or cosmetics on a skin or the like.

The air permeability of the stretchable laminated sheet of the present invention is preferably 10 to 100 $cm^3/cm^2 \cdot sec$ and more preferably 20 to 80 $cm^3/cm^2 \cdot sec$. In the case where the air permeability satisfies such ranges, evaporation or the like of the liquid component with which the stretchable laminated sheet is impregnated is reduced and the laminated sheet is prevented from drying. As a result, the durability of the effect obtainable by the drug solution or cosmetics can be improved.

According to the present invention, because the surface of the hydrophilic short fiber layer that is exposed on one of the surfaces of the stretchable laminated sheet has the concave and convex parts, stickiness of this sheet surface can be reduced, hence handleability is improved and excellent peeling property are obtained when stacking the laminated sheets together.

In addition, the surface of the microfiber layer that is exposed on the other surface of the laminated sheet is preferably flat so that excellent wearing feeling and adhesion property on the skin or other object can be attained.

The stretchable laminated sheet of the present invention is characterized in generating exceptionally excellent degree of elongation and stretchability, when the stretchable laminated sheet is used in a wet state rather than in the dry state. The characteristic that excellent degree of elongation and stretchability are not generated in the dry state has an industrially excellent effect in terms of an excellent distortion resistance against unexpected stress that is added during a production step prior to a step of impregnating the laminated sheet with the liquid component. More specifically, in a step of cutting the laminated sheet into an appropriate shape/size or shearing it for the purpose of applying the laminated sheet to a part of a body or face, the shape of the obtained sheet does not become misshapen, hence a desired shape can be faithfully achieved in the product.

When 100 parts by weight of the stretchable laminated sheet of the present invention is impregnated with 100 to 1500 parts by weight of the liquid component, an elongation recovery ratio is preferably in a range of 30 to 100% when the stretchable laminated sheet is extended in at least one direction by 30%. More preferably, the elongation recovery ratio is 50 to 100%.

Therefore, the stretchable laminated sheet of the present invention can be suitably used by impregnating it with the liquid component such as drug solution or cosmetics.

The drug solution or cosmetics with which the stretchable laminated sheet of the present invention can be impregnated are not particularly limited. Examples of the drug solution include an algefacient, deodorant, antibacterial agent, keratin softening agent, sebum discharge suppressant, keratolytic drug, bactericidal agent, sedative, antiphlogistic, disinfectant, insect pest repellent, brightening agent, degloss, healing agent, and protein remover. Examples of the cosmetics include liquid cosmetics such as a skin lotion, emulsion, and beauty essence having a moisturizer, cleansing component, antiperspirant component, aroma component, whitening ingredient, blood circulation promotion component, ultraviolet rays protective ingredient, or slimming ingredient.

Examples of the components of the drug solution or cosmetics with which the stretchable laminated sheet of the present invention is impregnated include polypeptide, such as collagenous polypeptide. Examples of the polypeptide include the ones disclosed in Japanese Patent Application Publication No. 2003-321500 and Japanese Patent Application Publication No. 2005-60314. Specific examples of the polypeptide include polypeptide expressed by a formula: R1-(X-Hyp-Gly)n-R2 or a formula: R1(Pro-Y-Gly)n-R2 (where X and Y are amino-acid residues, R1 is an H or other functional group, R2 is an OR3 or other functional group, R3 is an H or univalent metal, and n an integer).

The stretchable laminated sheet of the present invention has an exceptionally excellent characteristic in terms of the elongation recovery ratio obtained when impregnated with the liquid component, and the liquid component that is used for confirming the elongation recovery ratio may simply be water. Of course, the scope of the present invention includes a situation where the elongation recovery ratio is within a range of the values when other liquid components such as the drug solution or cosmetics are used.

In the stretchable laminated sheet of the present invention, regarding the degree of elongation in a direction in which the integrated hydrophilic short fiber layer produces extensibility, the ratio of the degree of elongation obtained when the laminated sheet is wet to the degree of elongation obtained when the laminated sheet is dry is preferably 1.1 to 2.0 times and more preferably 1.2 to 2.0 times. Note that "when the laminated sheet is dry" or "dry state" described in the present invention means that the laminated sheet is dried at 100° C. for at least 30 minutes. "When the laminated sheet is wet" or "wet state" mean that the laminated sheet is immersed in the liquid component for at least 10 minutes or that the 100 parts by weight of the sheet is impregnated with at least 100 parts by weight of the liquid component.

When the stretchable laminated sheet of the present invention is particularly in the wet state, it is slightly extended when applied to a skin or other object, and is then fitted moderately onto the skin or other object by the force that causes the sheet to shrink. Tightening feeling that is generated as the skin is moderately pulled by this force produces a comfortable wearing feeling and wearing stability.

In the stretchable laminated sheet of the present invention, 10% elongation modulus strength in the direction in which the integrated hydrophilic short fiber layer produces extensibility, or preferably in a direction perpendicular to the length direction of the unidirectionally-aligned fibers constituting the spunlace non-woven fabric contained in the integrated hydrophilic short fiber layer, is preferably 0.2 to 5.0 N/25 mm and more preferably 0.5 to 3.0 N/25 mm when the laminated sheet is in the dry state. Moreover, the 10% elongation modulus strength is preferably 0.1 to 4.0 N/25 mm and more preferably 0.2 to 2.5 N/25 mm when the laminated sheet is in the wet state. The ratio of the 10% elongation modulus strength in the wet state to the 10% elongation modulus strength in the dry state is preferably 0.1 to 0.9 times and more preferably 0.2 to 0.8 times.

The stretchable laminated sheet of the present invention can be used such that the microfiber layer is brought into contact with the skin or other object. In this case, the hydrophilic short fiber layer holds the drug solution or cosmetics, and the microfiber layer exudes a necessary amount of the drug solution or cosmetics to the skin or other object. The exuded amount or exuding speed can be adjusted. For example, the thickness of the microfiber layer can be reduced, the hydrophilic fibers can be mixed in the microfiber layer at an appropriate amount, and a hydrophilic agent can be added to resins configuring the microfiber layer or hydrophilizing processing can be performed, whereby the exuded amount and the exuding speed can be increased.

According to the present invention, in addition to the configuration in which the microfiber layer is constituted by fibers having small diameter, flexibility that is produced by including elastic elastomer fibers is an important factor that produces comfortable wearing feeling. Moreover, preferred fitting feeling, tightness, and wearing stability are obtained due to an appropriate gripping effect resulted from the viscosity of the elastomer fibers. The microfiber layer is constituted by fibers having small diameter to have a relatively high basis weight. In addition to this, adhesion property to the skin is improved due to the smooth surface of the microfiber layer brought into contact with the skin, whereby the masking effect or wrapping effect is attained, and the effects of the drug solution or cosmetics can be improved.

On the other hand, when the amount of drug solution or cosmetics is excessively high, excessively exuded drug solution or cosmetics form a layer of liquid between the smooth microfiber layer surface and the surface of the skin or other object, which makes the stretchable laminated sheet slippery on the surface of the skin or other object. As a result, the fitting properties might be impaired. In this case, the hydrophilic short fiber layer can be brought into contact with the skin or other object. Because the hydrophilic short fiber layer absorbs and holds the drug solution or cosmetics therein, the hydrophilic short fiber layer is capable of providing the cosmetics or drug solution to the skin or other object. In addition, the concave and convex parts formed on the hydrophilic fiber layer surface improve the slip properties of the sheet, whereby the fitting feeling is secured.

When the viscosity of the drug solution or cosmetics is relatively high, it might be beneficial to bring the hydrophilic fiber layer into contact with the skin or other object. Specifically, such a drug solution or cosmetics cannot penetrate through the microfiber layer easily and thus cannot reach the skin or other object sufficiently when the microfiber layer is brought into contact with the skin or other object. However, when the hydrophilic fiber layer is brought into contact with the skin or other object, the highly viscous of the drug solution or cosmetics can allow the stretchable laminated sheet to fit to the skin or other object. Moreover, the stretchable laminated sheet does not become sticky because the highly viscous drug solution or cosmetics cannot penetrate through the microfiber layer constituting the other surface of the laminated sheet. Therefore, good handling properties are attained.

The thickness of the stretchable laminated sheet of the present invention is not particularly limited. However, in terms of the impregnating ability and permeability of the drug solution or cosmetics, the thickness of the stretchable laminated sheet is preferably 0.2 to 0.7 mm when applying a load of 2 kg/cm$^2$ (0.196 MPa) to the stretchable laminated sheet. Flexibility required in the laminated sheet is appropriately selected in accordance with the retaining amount and viscosity of the drug solution or cosmetics, and the section to which the laminated sheet is applied.

According to the stretchable laminated sheet of the present invention, it is preferred that 100 parts by weight of the stretchable laminated sheet be impregnated with 100 to 1500 parts by weight of the drug solution or cosmetics.

The stretchable laminated sheet of the present invention can be suitably used in a product that is impregnated with the drug solution or cosmetics as described above.

The stretchable laminated sheet of the present invention can be impregnated with the drug solution or cosmetics and suitably applied to any part of a human boy, entire face, nose, eyes, lips, neck, arms, hands, fingers, hip, abdomen, thighs, calves, knees, and ankles. Specifically, the stretchable laminated sheet can be suitably used in a face mask, stretchable members for hygienic products such as a stretchable member for a disposable diaper, stretchable member for a diaper, stretchable member for a sanitary product, and stretchable member for a disposable diaper or diaper cover, a stretchable tape, band-aid, cotton gauze, supporter, sack, stretchable members for clothing, foundation cloth of a poultice, foundation cloth of a plaster material, foundation cloth of a slip stopper and the like.

EXAMPLES

Hereinafter, the present invention is described with examples, but the present invention is not limited to these examples.

A stretchable laminated sheet produced in each example and comparative examples was studied on various properties, and the definitions and method for measuring various properties are described hereinafter.

Note in the following description that "MD" means a direction that matches the length direction of the unidirectionally aligned fibers constituting a spunlace non-woven fabric of a used hydrophilic short fiber layer, and "CD" means a direction perpendicular to this direction.

(1) Average Fiber Diameter

A closeup picture of a surface of the non-woven fabric was taken using a scanning electron microscope (SEM) to measure the diameter of a hundred fibers, and the calculated average value was taken as an average fiber diameter.

(2) Pressure-Bonding Area Ratio

A closeup picture of a surface of the non-woven fabric was taken using the scanning electron microscope (SEM) to obtain a ratio of a pressure-bonding point per unit pressure-bonding pitch as a pressure-bonding area ratio.

Pressure-bonding area ratio (%)=(Area of pressure-bonding point occupying unit pitches/area of unit pitch)×100

(3) Elongation Recovery Ratio

The elongation recovery ratio was measured based on JIS L1096 "General Textile Testing Method." A test piece having a width of 25 mm and a length of 200 mm was cut out from the sheet such that the length direction of the test piece matches the direction perpendicular to the length direction in which the fibers constituting the spunlace non-woven fabric of the hydrophilic short fiber layer were aligned unidirectionally (CD direction).

This test piece was placed in a polyethylene pouch along with a sufficient amount of moisturizing toner (product name: Moistage, essence lotion, manufactured by Kracie Holdings Ltd.) in which the test piece can be immersed, and this pouch was left for 10 minutes. Hands were held over both surfaces of the test piece through the pouch three times to impregnate the test piece with the moisturizing toner until the dead weight of the test piece becomes no less than double, and the test piece was taken out of the pouch. A tensile tester autograph AG-G (product name, manufactured by Shimadzu Corporation) was used to set the gap between the zippers at 100 mm, whereby the test piece was fixed. The test piece was stretched to 30 mm at a tension rate of 300 mm/min, and thereafter shrunk back to the original size at the same rate, so that the load applied to the test piece is 0. Immediately thereafter, the test piece was stretched 30% at the same rate, and the stretched length where the load is applied again is taken as Lmm. The elongation recovery ratio was obtained based on the following equation.

Elongation recovery ratio when the test piece was stretched 30% (%)={(30*¹-L)/30*¹}×100

*¹: Length of the stretched test piece (mm)

(4) Rupture Strength and Elongation of the Laminated Sheet (Dry State Before the Sheet is Impregnated with the Drug Solution or Cosmetics)

The rupture strength and elongation were measured based on JIS L1906 "General Long Fiber Non-woven Fabric Testing Method." Test pieces having a width of 25 mm and a length of 200 mm were created. The two types of test pieces were obtained by cutting a sheet such that the length direction of one of the test pieces matches the length direction in which the fibers constituting the spunlace non-woven fabric of the hydrophilic short fiber layer are aligned unidirectionally (MD direction), and such that the length direction of the other test piece matches a direction perpendicular to the MD direction (CD direction). The tensile tester autograph AG-G (product name, manufactured by Shimadzu Corporation) was used to set the gap between the zippers at 100 mm, whereby the test pieces were fixed. The maximum strength and maximum elongation that are obtained until the test pieces were stretched and ruptured at a tension rate of 300 mm/min were taken as a rupture strength and a rupture elongation. The strength obtained when the test pieces were stretched 10% was taken as the 10% elongation modulus strength.

(5) Rupture Strength and Elongation of Wet Laminated Sheet (Wet State after the Sheet is Impregnated with the Drug Solution or Cosmetics)

The rupture strength and elongation were measured based on JIS L1906 "General Long Fiber Non-woven Fabric Testing Method." Two types of test pieces having a width of 25 mm and a length of 200 mm were prepared by cutting a sheet such that the length direction of one of the test pieces matches the MD direction and such that the length direction of the other test piece matches the CD direction in the same manner as (4) above. The test pieces were placed in a polyethylene pouch along with a sufficient amount of moisturizing toner (product name: Moistage, essence lotion, manufactured by Kracie Holdings Ltd.) in which the test piece can be immersed, and this pouch was left for 10 minutes. Hands were held over both surfaces of each test piece through the pouch three times to impregnate the test piece with the moisturizing toner until the dead weight of the test piece becomes no less than double, and the test pieces were taken out of the pouch. The tensile tester autograph AG-G (product name, produced by Shimadzu Corporation) was used to set the gap between the zippers at 100 mm, whereby the test pieces were fixed. The maximum strength and maximum elongation that are obtained until the test pieces were stretched and ruptured at a tension rate of 300 mm/min were taken as a rupture strength and a rupture elongation. The strength obtained when the test pieces were stretched 10% was taken as the 10% elongation modulus strength.

(6) Mass Per Unit Area

The mass per unit area was measured based on JIS L1906 "General Long Fiber Non-woven Fabric Testing Method." A test piece of 20 cm×20 cm was cut out from any five sections on the non-woven fabric. The weight of each of the test pieces was measured on an electronic balance, and the average weight was converted into parts by mass per 1 m² and taken as the mass per unit area.

(7) The Thickness of the Laminated Sheet, Thickness Ratio of Each Constituent Layer (%)

The thickness of the laminated sheet, thickness ratio of each constituent layer were measured based on JIS L1906 "General Long Fiber Non-woven Fabric Testing Method."

(i) The thickness L1 (mm) of the laminated sheet or of a dried clothes wearing sheet is measured.

(ii) The hydrophilic fiber layer and the microfiber layer are peeled, and the thickness L2 (mm) of the microfiber layer is measured.

(iii) The thickness L3 (mm) of the hydrophilic fiber layer is calculated by the following equation.

$L3$ (mm)=$L1$-$L2$ (iv) The thickness ratio R1 of the microfiber layer and the thickness R2 of the hydrophilic fiber layer based on the laminated sheet are calculated by the following equations.

$R1(\%)=L2/L1\times100$ $R2(\%)=L3/L1\times100$ (8) Wearing Stability

The laminated sheet was cut into the shape of a face mask, which was placed in a polyethylene pouch along with a sufficient amount of moisturizing toner (product name: Moistage, essence lotion, manufactured by Krade Holdings Ltd.) in which the test piece can be immersed, and this pouch was left for 10 minutes. Hands were held over both surfaces of the test piece through the pouch three times to impregnate the test piece with the moisturizing toner until the dead weight of the test piece becomes no less than double. As a result, a face mask was created.

Aside from this, the abovementioned moisturizing toner was added to a sheet that was cut into the shape of the same face mask in the same manner, and this sheet was impregnated with a moisturizing emulsion (product name: Moistage, essence lotion, manufactured by Kracie Holdings Ltd.) to create a face mask. These two types of face masks were put on the face of a panelist for 10 minutes, and the results of these two face masks were summed up to evaluate the adhesion property, the drying property, the skin tightness on three scales of ○, Δ, and x. Note in the present example that "good" "drying property" means that the moisturizing toner or the moisturizing emulsion in the laminated sheet does not evaporate easily off the laminated sheet.

○: Good

Δ: Somewhat weak x: Weak (9) Air Permeability

The air permeability of the laminated sheet or dried clothes wearing sheet was measured based on the Frazier method, JIS L1906 "General Long Fiber Non-woven Fabric Testing Method." A test piece of 200 mm×200 mm was prepared and the air permeability was measured using an air permeability tester (manufactured by Toyo Seiki Seisaku-sho Ltd.).

The codes and contents of the raw resins described in the tables below are as follows, the raw resins being used in the present invention.

A: Styrene-ethylene-butylene-styrene block copolymer, Clayton MD6705NS ((product name), manufactured by Clayton Polymer Co., Ltd.)
B: Propylene ethylene copolymer, VM2125 ((product name), manufactured by Exxon Mobile Corporation)
C: Thermoplastic polyurethane, Pandex T-1180 ((product name), manufactured by DIC-Bayer)
D: Polypropylene Mitsui polypro S119 ((product name), manufactured by Prime Polymer Co., Ltd.)
E: Ethylene octane copolymer, EG8402 ((product name), manufactured by Dow Chemical Co.)

Example 1

A meltblown non-woven fabric using A as the raw resin for the microfiber layer was used. As a meltblown device, a device configured by an extruder having a screw (with 30-mm diameter), heating body and gear pump, a spinneret (with 0.3-mm hole diameter, 501 holes, and 500-mm effective width), compressed-air generator, air heater, collecting conveyor having a polyester net, and winder was used. A was thrown into the extruder, heated/melted by the heating body at 230° C., discharged from the spinneret at a spinning speed of 0.45 g/min per unit hole. 98 kPa (gauge pressure) of compressed air that was heated at 400° C. was used to spray the discharged fiber onto the collecting conveyor having a polyester net that travels at a speed of 22 m/min. As a result, a meltblown non-woven fabric with randomly piled up fibers was obtained. The collecting conveyor was installed 25 cm away from the spinnerret cap. The sprayed air was removed by a suction device provided on the back of the collecting conveyor.

In the process of producing the meltblown non-woven fabric using the above method, a spunlace non-woven fabric of rayon/pump/rayon that is constituted by rayon having a fiber length of 51 mm and pulp having a fiber length of 7 mm, extensible in a direction perpendicular to the direction in which the fibers are aligned unidirectionally, and has a mass per unit area of 43 g/m² (laminated fiber layer having a weight ratio of 25/50/25) was inserted as the hydrophilic short fiber layer, and the 20 g/m² meltblown non-woven fabric was laminated thereon. Furthermore, thus obtained non-woven laminated fabric was subjected to partial thermocompression bonding using a point bond processor comprising an embossed roll having a concave and convex surface and a smooth roll, at a temperature of 80° C. and a pressure of 20 N/cm, such that the embossed roll comes into contact with the spunlace non-woven fabric. As a result, a laminated sheet in which a concaved area ratio was 25%, each concave area 0.46 mm², the depth 0.55 mm, and the distance between the concave parts 1.36 mm in a vertical direction and 2.72 mm in a horizontal direction was obtained. The thickness of the laminated sheet was 0.465 mm, and the microfiber layer consisted 25% and the hydrophilic fiber layer 75% of the laminated sheet, based on the thickness thereof. The properties of this laminated sheet are shown in Table 1.

The obtained laminated sheet had an excellent stretchability in the wet state.

Example 2

A meltblown non-woven fabric using A and B as the raw resins for the microfiber layer was used. As a meltblown device, a device configured by two extruders each having a screw (with 30-mm diameter), heating body and gear pump, a spinneret for mixed fibers (with 0.3-mm hole diameter, spinning holes for discharging different types of fibers that are aligned alternately in each row, 501 holes, and 500-mm effective width), compressed-air generator, air heater, collecting conveyor having a polyester net, and winder was used. A and B were thrown into the extruders respectively, heated/melted by the heating body at 230° C., discharged from the spinneret at a spinning speed of 0.45 g/min per unit hole A, B by setting the gear pump so that the ratio of A/B (weight %) becomes 50/50. 98 kPa (gauge pressure) of compressed air that was heated at 400° C. was used to spray the discharged fibers onto the collecting conveyor having a polyester net that travels at a speed of 22 m/min. As a result, a meltblown non-woven fabric with randomly and evenly piled up A fiber and B fiber was obtained. The collecting conveyor was installed 25 cm away from the spinneret. The sprayed air was removed by a suction device provided on the back of the collecting conveyor.

In the process of producing the meltblown non-woven fabric using the above method, a spunlace non-woven fabric used in Example 1 was inserted as the hydrophilic short fiber layer, and the 20 g/m² meltblown non-woven fabric was laminated thereon. The same processing as Example 1 was performed to obtain a laminated sheet. In thus obtained laminated sheet, the concaved area ratio was 25%, each concave area 0.46 mm², the depth 0.55 mm, and the distance between the concave parts was 1.36 mm in a vertical direction and 2.72 mm in a horizontal direction. The thickness of the laminated sheet was 0.484 mm, and the microfiber layer consisted 26% and the hydrophilic fiber layer 74% of the laminated sheet, based on the thickness thereof. The properties of this laminated sheet are shown in Table 1. The obtained laminated sheet had an excellent stretchability in the wet state.

Example 3

Other than the process of using a meltblown non-woven fabric in which B and C are used as the raw resins for the microfiber layer, the same processing as Example 2 was performed to obtain a laminated sheet. In thus obtained laminated sheet, the concaved area ratio was 25%, each concave area 0.46 mm², the depth 0.55 mm, and the distance between the concave parts was 1.36 mm in a vertical direction and 2.72 mm in a horizontal direction. The thickness of the laminated sheet was 0.411 mm, and the microfiber layer consisted 30% and the hydrophilic fiber layer 70% of the laminated sheet, based on the thickness thereof. The properties of this laminated sheet are shown in Table 1. The obtained laminated sheet had an excellent stretchability in the wet state.

Example 4

A meltblown non-woven fabric using B and E as the raw resins for the microfiber layer was used. As a meltblown device, a device configured by two extruders each having a screw (with 30-mm diameter), heating body and gear pump, a spinneret for mixed fibers (with 0.3-mm hole diameter, spinning holes for discharging different types of fibers that are aligned alternately in each row, 501 holes, and 500-mm effective width), compressed-air generator, air heater, collecting conveyor having a polyester net, and winder was used. B and E were thrown into the extruders respectively, heated/melted by the heating body at 230° C., discharged from the spinneret at a spinning speed of 0.45 g/min per unit hole B, E by setting the gear pump so that the ratio of B/E (weight %) becomes 50/50. 98 kPa (gauge pressure) of compressed air that was heated at 400° C. was used to spray the discharged fibers onto the collecting conveyor having a polyester net that travels at a speed of 22 m/min. As a result, a meltblown non-woven fabric with randomly and evenly piled up B fiber and E fiber was obtained. The collecting conveyor was installed 25 cm away from the spinneret. The sprayed air was removed by a suction device provided on the back of the collecting conveyor.

In the process of producing the meltblown non-woven fabric using the above method, a spunlace non-woven fabric used in Example 1 was inserted as the hydrophilic short fiber layer, and the 20 g/m$^2$ meltblown non-woven fabric was laminated thereon. The same processing as Example 1 was performed to obtain a laminated sheet. In thus obtained laminated sheet, the concaved area ratio was 25%, each concave area 0.46 mm$^2$, the depth 0.55 mm, and the distance between the concave parts was 1.36 mm in a vertical direction and 2.72 mm in a horizontal direction. The thickness of the laminated sheet was 0.385 mm, and the microfiber layer consisted 28% and the hydrophilic fiber layer 72% of the laminated sheet, based on the thickness thereof. The properties of this laminated sheet are shown in Table 2. The obtained laminated sheet had an excellent stretchability in the wet state.

Example 5

A meltblown non-woven fabric was used based on Example 4.

In the process of producing the meltblown non-woven fabric using the above method, a spunlace non-woven fabric of rayon/polyester that is constituted by rayon having a fiber length of 51 mm and polyester having a fiber length of 51 mm, extensible in a direction perpendicular to the direction in which the fibers are aligned unidirectionally, and has a mass per unit area of 43 g/m$^2$ (mixed cotton having a weight ratio of 40/60) was inserted as the hydrophilic short fiber layer, and the 20 g/m$^2$ meltblown non-woven fabric was laminated thereon. Furthermore, thus obtained non-woven laminated fabric was subjected to partial thermocompression bonding using the point bond processor comprising an embossed roll having an concave and convex surface and a smooth roll, at a temperature of 80° C. and a pressure of 20 N/cm, such that the embossed roll comes into contact with the spunlace non-woven fabric. As a result, a laminated sheet in which a concaved area ratio was 25%, each concave area 0.46 mm$^2$, the depth 0.55 mm, and the distance between the concave parts 1.36 mm in a vertical direction and 2.72 mm in a horizontal direction was obtained. The thickness of the laminated sheet was 0.324 mm, and the microfiber layer consisted 33% and the hydrophilic fiber layer 67% of the laminated sheet, based on the thickness thereof. The properties of this laminated sheet are shown in Table 2. The obtained laminated sheet had an excellent stretchability in the wet state.

Example 6

A meltblown non-woven fabric was used based on Example 2.

In the process of producing the meltblown non-woven fabric using the above method, a spunlace non-woven fabric that is constituted by rayon having a fiber length of 51 mm, extensible in a direction perpendicular to the direction in which the fibers are aligned unidirectionally, and having a mass per unit area of 43 g/m$^2$ was inserted as the hydrophilic short fiber layer, and the 20 g/m$^2$ meltblown non-woven fabric was laminated thereon. Furthermore, thus obtained non-woven laminated fabric was subjected to partial thermocompression bonding using the point bond processor comprising an embossed roll having an concave and convex surface and a smooth roll, at a temperature of 80° C. and a pressure of 20 N/cm, such that the embossed roll comes into contact with the spunlace non-woven fabric. As a result, a laminated sheet in which a concaved area ratio was 25%, each concave area 0.46 mm$^2$, the depth 0.55 mm, and the distance between the concave parts 1.36 mm in a vertical direction and 2.72 mm in a horizontal direction was obtained. The thickness of the laminated sheet was 0.468 mm, and the microfiber layer consisted 26% and the hydrophilic fiber layer 74% of the laminated sheet, based on the thickness thereof. The properties of this laminated sheet are shown in Table 2. The obtained laminated sheet had an excellent stretchability in the wet state.

The laminated sheet obtained in each of Examples 1 to 6 was impregnated with the moisturizing toner or moisturizing emulsion and used as a beauty face mask. As a result, the wearing stability to the face was good when both the hydrophilic short fiber layer and the microfiber layer were applied to the skin. The results are shown in Tables 1 and 2.

Comparative Example 1

The spunlace non-woven fabric used as the hydrophilic short fiber layer in Example 1 was used as a single layer not laminated with the microfiber layer. The results are shown in Table 3. This fabric was weak in stretchability in the wet state.

Comparative Example 2

A meltblown non-woven fabric using D as the raw material for the microfiber layer was used. The microfiber layer and the hydrophilic short fiber layer were subjected to spunlace treatment on a 100-mesh plain weave conveyor net by means of a nozzle having an orifice diameter of 0.3 mm and an orifice interval of 0.5 mm under the condition of 1 MPa water pressure. Other than this processing, the same processing as Example 1 was performed to obtain a laminated sheet. The results are shown in Table 3. This sheet was weak in stretchability and high in air permeability in the wet state. Therefore, the drug solution or cosmetics with which the fabric was impregnated evaporated easily.

Comparative Example 3

A polyethylene/polyethylene terephthalate splittable fibers (product name: Sepa, manufactured by Daiwabo Co., Ltd.) were used in the microfiber layer, and the spunlace non-woven fabric used as the hydrophilic short fiber layer in Example 1 was used to perform the spunlace treatment on this micro fiber layer and hydrophilic short fiber layer on a 100-mesh plain weave conveyor net by means of a nozzle having an orifice diameter of 0.3 mm and an orifice interval of 0.5 mm under the condition of 1 MPa water pressure. Consequently, a laminated sheet was obtained. The results are shown in Table 3. This sheet was weak in stretchability and high in air permeability in the wet state. Therefore, the drug solution or cosmetics with which the fabric was impregnated evaporated easily.

The laminated sheet obtained in each of Comparative Examples 1 to 3 was impregnated with the moisturizing toner or moisturizing emulsion and used as a beauty face mask. As a result, weak wearing stability was obtained because of no stretchability generated in the non-woven fabric. The results are shown in Table 3.

TABLE 1

| | | | Example 1 | Example 2 | Example 3 |
|---|---|---|---|---|---|
| Microfiber layer | Raw material 1 | | A | A | B |
| | Raw material 2 | | — | B | C |
| | Weight ratio (raw materials 1:2) | | 100:0 | 50:50 | 50:50 |
| | Configuration of fiber | | Regular | Mixed fibers | Mixed fibers |
| | Production method | | Meltblown | Meltblown | Meltblown |
| | Fineness | μm | 10 | 10 | 10 |
| | Mass per unit area | g/m² | 20 | 20 | 20 |
| Hydrophilic short fiber layer | Raw material 1 | | Rayon | Rayon | Rayon |
| | Raw material 2 | | Pulp | Pulp | Pulp |
| | Raw material 3 | | Rayon | Rayon | Rayon |
| | Weight ratio (raw materials 1:2:3) | | 25:50:25 | 25:50:25 | 25:50:25 |
| | Production method | | Spunlace | Spunlace | Spunlace |
| | Structure | | Laminated | Laminated | Laminated |
| | Mass per unit area | g/m² | 43 | 43 | 43 |
| | Strength in dry state (MD/CD) | N/25 mm | 17/9.7 | 17/9.7 | 17/9.7 |
| | Elongation in dry state (MD/CD) | % | 21/56 | 21/56 | 21/56 |
| | 10% elongation modulus strength in dry state (MD/CD) | N/25 mm | 2.4/1.3 | 2.4/1.3 | 2.4/1.3 |
| | Strength in wet state (MD/CD) | N/25 mm | 7.3/4.4 | 7.3/4.4 | 7.3/4.4 |
| | Elongation in wet state (MD/CD) | % | 39/52 | 39/52 | 39/52 |
| | 10% elongation modulus strength in wet state (MD/CD) | N/25 mm | 1.0/0.6 | 1.0/0.6 | 1.0/0.6 |
| | Air permeability (cm³/cm²/sec) | | 170 | 170 | 170 |
| Laminated sheet | Lamination method | | Emboss | Emboss | Emboss |
| | Thickness of laminated sheet | mm | 0.465 | 0.484 | 0.411 |
| | Thickness of microfiber layer/Ratio based on laminated sheet | mm/% | 0.116/25 | 0.126/26 | 0.121/30 |
| | Thickness of hydrophilic fiber layer/Ratio based on laminated sheet | mm/short % | 0.349/75 | 0.358/74 | 0.290/70 |
| | Strength in dry state (MD/CD) | N/25 mm | 14/7.2 | 15/7.6 | 14/7.8 |
| | Elongation in dry state (MD/CD) | % | 24/66 | 23/64 | 21/61 |
| | 10% elongation modulus strength in dry state (MD/CD) | N/25 mm | 3.7/1.9 | 3.8/1.9 | 3.8/1.9 |
| | Strength in wet state (MD/CD) | N/25 mm | 6.3/3.8 | 6.9/4.0 | 6.5/4.2 |
| | Elongation in wet state (MD/CD) | % | 39/83 | 41/79 | 38/76 |
| | 10% elongation modulus strength in wet state (MD/CD) | N/25 mm | 0.9/0.5 | 1.0/0.5 | 1.0/0.5 |
| | 30% elongation recovery ratio (CD) in wet state | % | 97 | 93 | 93 |
| | Air permeability (cm³/cm²/sec) | | 62 | 57 | 59 |
| | Wearing stability*1 | Adhesion property | ○(skin: hydrophilic) Δ: (skin: microfiber) | ○(skin: hydrophilic) ○(skin: microfiber) | ○(skin: hydrophilic) ○(skin: microfiber) |
| | | Drying property | ○(skin: hydrophilic) ○(skin: microfiber) | ○(skin: hydrophilic) ○(skin: microfiber) | ○(skin: hydrophilic) ○(skin: microfiber) |

TABLE 1-continued

|  | Example 1 | Example 2 | Example 3 |
|---|---|---|---|
| Tightness | ○(skin: hydrophilic) ○(skin: microfiber) | ○(skin: hydrophilic) ○(skin: microfiber) | ○(skin: hydrophilic) ○(skin: microfiber) |

*[1]Skin: Hydrophilic . . . Hydrophilic short fiber layer is applied to the skin. Skin: Microfiber . . . Microfiber layer is applied to the skin.

TABLE 2

|  |  |  | Example 4 | Example 5 | Example 6 |
|---|---|---|---|---|---|
| Microfiber layer | Raw material 1 |  | B | B | A |
|  | Raw material 2 |  | E | E | B |
|  | Weight ratio (raw materials 1:2) |  | 50:50 | 50:50 | 50:50 |
|  | Configuration of fiber |  | Mixed fibers | Mixed fibers | Mixed fibers |
|  | Production method |  | Meltblown | Meltblown | Meltblown |
|  | Fineness | μm | 10 | 10 | 10 |
|  | Mass per unit area | g/m² | 20 | 20 | 20 |
| Hydrophilic short fiber layer | Raw material 1 |  | Rayon | Rayon | Rayon |
|  | Raw material 2 |  | Pulp | Polyester | — |
|  | Raw material 3 |  | Rayon | — | — |
|  | Weight ratio (raw materials 1:2:3) |  | 25:50:25 | 40:60:0 | 100:0:0 |
|  | Production method |  | Spunlace | Spunlace | Spunlace |
|  | Structure |  | Laminated | Mixed cotton | Single layer |
|  | Mass per unit area | g/m² | 43 | 43 | 43 |
|  | Strength in dry state (MD/CD) | N/25 mm | 17/9.7 | 25/8.1 | 17/9.4 |
|  | Elongation in dry state (MD/CD) | % | 21/56 | 45/65 | 25/55 |
|  | 10% elongation modulus strength in dry state (MD/CD) | N/25 mm | 2.4/1.3 | 4.0/1.1 | 2.6/1.5 |
|  | Strength in wet state (MD/CD) | N/25 mm | 7.3/4.4 | 17/5.7 | 7.0/4.1 |
|  | Elongation in wet state (MD/CD) | % | 39/52 | 45/63 | 35/54 |
|  | 10% elongation modulus strength in wet state (MD/CD) | N/25 mm | 1.0/0.6 | 2.4/0.6 | 1.2/0.4 |
|  | Air permeability (cm³/cm²/sec) |  | 170 | 120 | 160 |
| Laminated sheet | Lamination method |  | Emboss | Emboss | Emboss |
|  | Thickness of laminated sheet | mm | 0.385 | 0.324 | 0.468 |
|  | Thickness of microfiber layer/Ratio based on laminated sheet | mm/% | 0.108/28 | 0.107/33 | 0.125/26 |
|  | Thickness of hydrophilic short fiber layer/Ratio based on laminated sheet | mm/% | 0.277/72 | 0.217/67 | 0.343/74 |
|  | Strength in dry state (MD/CD) | N/25 mm | 16/7.1 | 23/6.1 | 15/8.5 |
|  | Elongation in dry state (MD/CD) | % | 21/68 | 43/74 | 20/57 |
|  | 10% elongation modulus strength in dry state (MD/CD) | N/25 mm | 5.2/1.7 | 4.1/1.2 | 4.1/1.8 |
|  | Strength in wet state (MD/CD) | N/25 mm | 7.1/4.6 | 20/6.0 | 7.1/4.5 |
|  | Elongation in wet state (MD/CD) | % | 37/82 | 42/81 | 41/91 |
|  | 10% elongation modulus strength in wet state (MD/CD) | N/25 mm | 2.6/0.5 | 2.5/0.6 | 1.4/0.6 |

TABLE 2-continued

|  |  |  | Example 4 | Example 5 | Example 6 |
|---|---|---|---|---|---|
| 30% elongation recovery ratio (CD) in wet state | | % | 92 | 93 | 94 |
| Air permeability (cm³/cm²/sec) | | | 60 | 53 | 51 |
| Wearing stability*¹ | Adhesion property | | ○(skin: hydrophilic) ○(skin: microfiber) | ○(skin: hydrophilic) ○(skin: microfiber) | ○(skin: hydrophilic) ○(skin: microfiber) |
| | Drying property | | ○(skin: hydrophilic) ○(skin: microfiber) | ○(skin: hydrophilic) ○(skin: microfiber) | ○(skin: hydrophilic) ○(skin: microfiber) |
| | Tightness | | ○(skin: hydrophilic) ○(skin: microfiber) | ○(skin: hydrophilic) ○(skin: microfiber) | ○(skin: hydrophilic) ○(skin: microfiber) |

*¹Skin: Hydrophilic . . . Hydrophilic short fiber layer is applied to the skin. Skin: Microfiber . . . Microfiber layer is applied to the skin.

TABLE 3

|  |  |  | Comparative Example 1 | Comparative Example 2 | Comparative Example 3 |
|---|---|---|---|---|---|
| Microfiber layer | Raw material 1 | | — | D | Polyester |
| | Raw material 2 | | — | — | Polyethylene |
| | Weight ratio (raw materials 1:2) | | 0 | 100:0 | 50:50 |
| | Configuration of fiber | | — | Regular | Splittable |
| | Production method | | — | Meltblown | Card |
| | Fineness | μm | — | 5 | 16 (8 splits) |
| | Mass per unit area | g/m² | — | 20 | 15 |
| Hydrophilic short fiber layer | Raw material 1 | | Rayon | Rayon | Rayon |
| | Raw material 2 | | Pulp | Pulp | Pulp |
| | Raw material 3 | | Rayon | Rayon | Rayon |
| | Weight ratio (raw materials 1:2:3) | | 25:50:25 | 25:50:25 | 25:50:25 |
| | Production method | | Spunlace | Spunlace | Spunlace |
| | Structure | | Laminated | Laminated | Laminated |
| | Mass per unit area | g/m² | 43 | 43 | 43 |
| | Strength in dry state (MD/CD) | N/25 mm | 17/9.7 | 17/9.7 | 17/9.7 |
| | Elongation in dry state (MD/CD) | % | 21/56 | 21/56 | 21/56 |
| | 10% elongation modulus strength in dry state (MD/CD) | N/25 mm | 2.4/1.3 | 2.4/1.3 | 2.4/1.3 |
| | Strength in wet state (MD/CD) | N/25 mm | 7.3/4.4 | 7.3/4.4 | 7.3/4.4 |
| | Elongation in wet state (MD/CD) | % | 39/52 | 39/52 | 39/52 |
| | 10% elongation modulus strength in wet state (MD/CD) | N/25 mm | 1.0/0.6 | 1.0/0.6 | 1.0/0.6 |
| | Air permeability (cm³/cm²/sec) | | 170 | 170 | 170 |
| Laminated sheet | Lamination method | | — | Spublace | Spulace |
| | Thickness of laminated sheet | mm | — | 0.402 | 0.526 |
| | Thickness of microfiber layer/ Ratio based on laminated sheet | mm/ % | — | 0.104/26 | 0.224/42.6 |
| | Thickness of hydrophilic short fiber layer/Ratio based on laminated sheet | mm/ % | 0.453/— | 0.298/74 | 0.302/57.4 |
| | Strength in dry state (MD/CD) | N/25 mm | — | 14/7.2 | 15/8.3 |

TABLE 3-continued

| | | Comparative Example 1 | Comparative Example 2 | Comparative Example 3 |
|---|---|---|---|---|
| Elongation in dry state (MD/CD) | % | — | 20/50 | 22/57 |
| 10% elongation modulus strength in dry state (MD/CD) | N/25 mm | — | 3.7/2.0 | 4.0/2.1 |
| Strength in wet state (MD/CD) | N/25 mm | — | 6.0/4.1 | 6.8/4.2 |
| Elongation in wet state (MD/CD) | % | — | 35/51 | 34/58 |
| 10% elongation modulus strength in wet state (MD/CD) | N/25 mm | — | 1.1/0.5 | 1.2/0.6 |
| 30% elongation recovery ratio (CD) in wet state | % | 3 | 6 | 3 |
| Air permeability ($cm^3/cm^2/sec$) | | — | 150 | 140 |
| Wearing stability*[1] | Adhesion property | Δ | ○(skin: hydrophilic) Δskin: microfiber) | ○(skin: hydrophilic) Δ(skin: microfiber) |
| | Drying property | x | ○(skin: hydrophilic) x(skin: microfiber) | ○(skin: hydrophilic) x(skin: microfiber) |
| | Tightness | x | x(skin: hydrophilic) x(skin: microfiber) | x(skin: hydrophilic) x(skin: microfiber) |

*[1]Skin: Hydrophilic . . . Hydrophilic short fiber layer is applied to the skin. Skin: Microfiber . . . Microfiber layer is applied to the skin.

INDUSTRIAL APPLICABILITY

The stretchable laminated sheet of the present invention can be impregnated with the drug solution or cosmetics and suitably applied to any part of a human boy, entire face, nose, skin around eyes, lips, neck, arms, hands, fingers, hip, abdomen, thighs, calves, knees, and ankles. Specifically, the stretchable laminated sheet can be suitably used in, for example, a face mask, stretchable members for hygienic products such as a stretchable member for a disposable diaper, stretchable member for a diaper, stretchable member for a sanitary product, and stretchable member for a disposable diaper or diaper cover, a stretchable tape, band-aid, cotton gauze, supporter, sack, stretchable members for clothing, foundation cloth of a poultice, foundation cloth of a plaster material, foundation cloth of a slip stopper and the like. However, the application of the stretchable laminated sheet of the present invention is not limited to the above applications.

What is claimed is:

1. A method of manufacturing a stretchable laminated sheet, comprising:
    laminating and partially thermocompression-bonding a hydrophilic short fiber layer and a microfiber layer,
    wherein the hydrophilic short fiber layer is extensible in at least one direction,
    the microfiber layer comprises: an elastomer long fiber having a fiber diameter in a range of 15 μm or less in an amount in a range of 50% or more by weight relative to the microfiber layer; and a non-elastomer fiber having a fiber diameter in a range from 1 to 15 μm in an amount in a range from 1 to 50% by weight relative to the microfiber layer,
    the partially thermocompression-bonding comprises forming concave-and-convex parts on a surface of the hydrophilic short fiber layer, wherein concave parts in the concave-and-convex parts are discontinuous and regular,
    the hydrophilic short fiber layer is exposed on a surface of a stretchable laminated sheet formed with the hydrophilic short fiber layer and the microfiber layer,
    a total area of the concave parts of the concave-and-convex parts is in a range from 3 to 40% of an area of the surface of the hydrophilic short fiber layer,
    the partially thermocompression-bonding comprises integrating the hydrophilic short fiber layer and the microfiber layer at least by softening the elastomer long fiber of the microfiber layer and consequently bonding the elastomer long fiber with a fiber constituting the hydrophilic short fiber layer in a sheet in a thickness direction of a section where the concave parts are formed,
    the partially thermocompression-bonding is performed by using a heating emboss roll,
    the elastomer long fiber comprises at least one resin selected from the group consisting of a styrene elastomer and an urethane elastomer, and
    the stretchable laminated sheet has an elongation recovery ratio in a range from 30 to 100%, wherein the elongation recovery ratio is measured by impregnating the stretchable laminated sheet with at least 100 and not more than 1500 parts by weight of a liquid component relative to 100 parts by weight of the stretchable laminated sheet and measuring the elongation recovery after the liquid-impregnated stretchable laminated sheet is extended by 30% in at least one direction.

2. The method according to claim 1, wherein the microfiber layer is exposed on a surface of the stretchable laminated sheet opposite to the surface to which the hydrophilic short fiber layer is exposed and is smooth.

3. The method according to claim 1, wherein the hydrophilic short fiber layer has at least 30% by weight of a short fiber comprising at least one fiber selected from the group consisting of cotton, rayon, cuprammonium, pulp, and two or more of thereof.

4. The method according to claim 1, wherein the hydrophilic short fiber layer is a spunlace non-woven fabric or a wetlaid web.

5. The method according to claim 1, wherein the microfiber layer is a fiber layer comprising randomly accumulating long fibers produced by a melt blow method.

6. The method according to claim 1, wherein the stretchable laminated sheet is impregnated with drug solution or cosmetics in a ratio in a range from 100 to 1500 parts by weight of the drug solution or cosmetics relative to 100 parts by weight of the stretchable laminated sheet.

7. A method of manufacturing a product, comprising:
manufacturing the stretchable laminated sheet by using the method according to claim 1, and obtaining a product from the stretchable laminated sheet.

8. The method according to claim 7, wherein the product is a facemask.

9. The method according to claim 1, wherein the elastomer long fiber is made of at least one resin selected from the group consisting of styrene-ethylene-butylene-styrene block copolymer and thermoplastic polyurethane.

10. The method according to claim 1, wherein a thickness of the microfiber layer is in a range of 80% or less relative to a thickness of the stretchable laminated sheet.

11. The method according to claim 1, wherein an area of each of the concave parts is in a range from 0.15 to 15 $mm^2$.

12. The method according to claim 1, wherein a distance between the concave parts is in a range from 0.5 to 20 mm.

13. The method according to claim 1, wherein a thickness of the stretchable laminated sheet is in a range from 0.2 to 0.7 mm, when measured by applying a load of 2 $kg/cm^2$, which is equivalent to 0.196 MPa, to the stretchable laminated sheet.

* * * * *